US005515841A

United States Patent [19]
Robertson et al.

[11] Patent Number: 5,515,841
[45] Date of Patent: May 14, 1996

[54] INHALER

[75] Inventors: Paul A. Robertson, Chrishall; Eric A. Baum; David J. Greenleaf, both of Loughborough, all of England

[73] Assignee: Minnesota Mining and Manufacturing Company, St. Paul, Minn.

[21] Appl. No.: 343,030

[22] Filed: Nov. 21, 1994

[30] Foreign Application Priority Data

Nov. 25, 1993 [GB] United Kingdom .................. 9324250

[51] Int. Cl.$^6$ .............................. A61M 11/00; B05B 3/14
[52] U.S. Cl. .............................. 128/200.16; 128/200.14; 128/200.18; 128/200.21; 239/102.2
[58] Field of Search ......................... 128/200.16, 200.18, 128/200.21, 200.22, 200.23, 203.12, 204.13, 200.14; 239/102.2

[56] References Cited

U.S. PATENT DOCUMENTS

| | | | |
|---|---|---|---|
| 3,729,138 | 4/1973 | Tysk | 239/102.2 |
| 3,746,000 | 7/1973 | Edwards | 128/194 |
| 4,094,317 | 6/1978 | Wasnich | 128/200.16 |
| 4,319,155 | 3/1982 | Nakai et al. | 310/316 |
| 5,134,993 | 8/1992 | van der Linden et al. | 128/200.14 |
| 5,152,456 | 10/1992 | Ross et al. | 128/200.16 |
| 5,261,601 | 11/1993 | Ross et al. | 239/102.2 |
| 5,299,739 | 4/1994 | Takahashi et al. | 239/102.2 |

FOREIGN PATENT DOCUMENTS

| | | | |
|---|---|---|---|
| 0174033 | 12/1986 | European Pat. Off. | 128/200.16 |
| 2272389 | 5/1994 | United Kingdom | B05B 11/02 |
| WO92/11050 | 7/1992 | WIPO | A61M 15/00 |
| WO95/15822 | 6/1995 | WIPO | B05B 17/06 |

OTHER PUBLICATIONS

European Search Report dated Aug. 17, 1995.
Copy of U.K. Search Report dated Jan. 26, 1994.

*Primary Examiner*—Edgar S. Burr
*Assistant Examiner*—V. Srivastava
*Attorney, Agent, or Firm*—Gary L. Griswold; Walter N. Kirn; Dale E. Hulse

[57] ABSTRACT

An inhalation device including an aerosol generator for dispensing droplets of liquid medicament comprising a housing defining a liquid receptacle having an opening, a nozzle arrangement comprising a plurality of orifices, vibrating means for vibrating the nozzle arrangement, and means for introducing the liquid medicament on the outer surface of the nozzle arrangement. Control means are also provided for controlling the vibrating means such that when the liquid medicament is introduced on the outer surface of the nozzle arrangement, the nozzle arrangement may be vibrated to cause the liquid to enter the liquid receptacle through the orifices and thereafter be expelled from the orifices through the outer surface of the nozzle arrangement in the form of atomised droplets.

8 Claims, 1 Drawing Sheet

INHALER

FIELD OF THE INVENTION

This invention relates to inhalers for the delivery of therapeutic substances to the respiratory system of a patient and in particular to inhalers which deliver the therapeutic substance in the form of a liquid as a dispersion of fine droplets.

BACKGROUND

Since the metered dose pressurised inhaler was introduced in the mid-1950's, inhalation has become the most widely used route for delivering bronchodilators, offering a rapid onset of action and a low instance of systemic side effects. More recently, inhalation from a pressurised inhaler has been a route selected for the administration of other drugs, e.g., ergotamine, which are not primarily concerned with the treatment of a bronchial malady.

The metered dose inhaler is dependent upon the propulsive force of a propellant system used in its manufacture. The propellant generally comprises a mixture of liquified chlorofluorocarbons (CFC's) which are selected to provide the desired vapour pressure and stability of the formulation. Propellants 11, 12 and 114 are the most widely used propellants in aerosol formulations for inhalation administration.

In recent years it has been established that CFC's react with the ozone layer around the earth and contribute towards its depletion. There has been considerable pressure around the world to reduce substantially the use of CFC's and various Governments have banned the "non-essential" use of CFC's. Such "nonessential" uses include the use of CFC's as refrigerants and blowing agents, but heretofore the use of CFC's in medicines, which contributes to less than 1% of the total use of CFC's, has not been restricted. Nevertheless, in view of the adverse effect of CFC's on the ozone layer it is desirable to seek alternative propellant systems which are suitable for use in inhalation aerosols or an inhaler which is capable of delivering drugs in such an efficacious manner without employing an aerosol propellant.

W092/11050 discloses an inhaler device for dispensing droplets of liquid medicament to a patient comprising a body having a mouth piece or nasal adaptor, and a reservoir of liquid medicament in communication with an aerosol generator, the aerosol generator comprising a chamber for liquid medicament and a nozzle arrangement comprising a plurality of orifices in fluid flow relationship with liquid medicament in said chamber, means for cyclically pressurising the liquid medicament in said chamber such that liquid from said chamber is periodically expelled through the orifices as atomised droplets of liquid medicament so they may be inhaled via the mouth piece or nasal adaptor, the inhaler additionally comprising dosage control means for deactivating the aerosol generator after a predetermined time or after a predetermined volume of liquid medicament has been expelled from the chamber. The cyclic pressurisation may be achieved utilising a piezo-electric element which is caused to vibrate ultrasonically and acts directly or indirectly on the liquid.

In one embodiment of W092/11050 the nozzle assembly is vibrated. The nozzle assembly may be flexible and comprise a piezo-electric element, e.g., in the form of a ring attached to the nozzle array extended around the orifices, such that when the piezo-electric element is excited it causes vibration of the nozzle arrangement at ultrasonic frequencies resulting in cyclic pressurisation of the liquid in the chamber and ejection of droplets of liquid through the orifices.

In a further embodiment of W092/11050 the nozzle assembly is vibrated by a vibrator element comprising a piezo-electric ring secured to a metal disc of larger diameter, the vibrating element having a central aperture through which droplets from the nozzle array are emitted. The vibrating element is preferably secured only over its central portion, either directly to the nozzle array or to the housing of the chamber in close proximity to the nozzle array e.g. over a central portion of about 4 mm diameter, such that ultrasonic energy is transferred directly to the nozzle array. This arrangement allows the outer area of the vibrating element, which is typically about 20 mm diameter, to vibrate freely as a resonator and enables aerosol generation to occur with an input power to the piezo-electric element of about 0.5 W. Also the arrangement has less tendency to draw tiny air bubbles in through the nozzles during operation, since this reduces the tendency for and effects of, vibrational mode hopping which can occur if the piezo driver is attached around its periphery.

During testing such a device, it was discovered that when seepage is allowed to occur to the extent of producing a small drop on the external surface of the nozzle array, subsequent excitation of the piezo transducer does not immediately generate a stream of droplets. Instead, there is a brief delay before atomisation commences while the drop is drawn back into the liquid chamber under the influence of the vibrating nozzles. Furthermore, if the liquid chamber is empty and a drop is deliberately placed on the nozzle array, the same effect is observed: the drop is drawn in through the array and subsequently atomised into primary monodispersed droplets. This phenomenon can be utilised in an alternative construction of an inhaler.

SUMMARY OF THE INVENTION

Therefore, according to the present invention there is provided an inhalation device for dispensing droplets of liquid medicament to a patient comprising a body having a mouthpiece or nasal adaptor, a liquid receptacle having an opening covered by a nozzle arrangement, the nozzle arrangement comprising a plurality of orifices and having an inner surface facing the interior of the liquid receptacle and an outer surface, vibrating means for vibrating the nozzle arrangement, means for introducing liquid medicament on the outer surface of the nozzle arrangement and control means for controlling the vibrating means such that when liquid medicament is introduced on the outer surface of the nozzle arrangement the nozzle arrangement may be vibrated to cause the liquid to enter the orifices and thereafter be expelled from the orifices through the outer surface in the form of atomised droplets.

In general a dose of liquid medicament will be introduced on the outer surface of the nozzle arrangement having a volume in excess of the volume of the orifices and the liquid is caused to enter the liquid receptacle through the orifices and thereafter is expelled from the liquid receptacle through the orifices.

The inhaler of the invention may be used to dispense single shots of medication without the need for an integral in-line dose gauge or reservoir. The dose to be dispensed would be metered onto the nozzle array, which is vibrated e.g. by a piezo-electric transducer, the liquid drawn in automatically and subsequently atomised. Thus, the inhaler is useful for dispensing single or a low number of doses of, for example, an expensive biotechnology molecule for which inhalers employing a reservoir of a hundred or more doses would be unsuitable.

The means for introducing medicament on the nozzle may be separate from the remainder of the inhaler. For example, the system could contain ampoules of individual doses or be a reservoir from which individual doses could be dispersed, e.g. micro-syringe and pump. Alternatively the system could be an integral part of the device and designed to dispense a drop onto the nozzle array as and when required. Such a system is described in DE 3608621 and is used in the Respimat inhaler as developed by Boehringer Ingelheim (Journal of Biopharmaceutical Sciences Vol. 3 (½) 85–90, DE 3627222, DE 3616713).

Suitable nozzle arrangements and vibrating means, e.g. piezo-electric transducers, are disclosed in WO92/11050, the entire contents of which are incorporated herein by reference. The inhaler of the invention additionally comprises a mouthpiece or nasal adaptor and may include a venturi arrangement and breath-actuation mechanism as disclosed in WO92/11050.

It has been found that the amplitude or frequency of the voltage signal applied to the piezo-electric transducer vibrating the nozzle arrangement to draw in liquid can be different to that required to induce atomisation. For example, a lower amplitude signal will draw in liquid but will not induce subsequent atomisation. This offers the opportunity to delay the onset of atomisation until required, when the voltage signal is adjusted by increasing the amplitude and/or changing the applied frequency.

Thus, the option to draw in liquid and atomise immediately or to draw in and retain for subsequent atomisation can be predetermined and executed by appropriate control of the amplitude and/or frequency of the excitation voltage applied to the piezoelectric transducer. Low voltage will draw liquid into the device, higher voltage will guarantee its subsequent atomisation. Such an amplitude change may be replaced or supported by an appropriate change of frequency to induce the same effect of atomisation. This feature enables the device to be primed with liquid prior to it being required for therapeutic use thus ensuring, if required, immediate atomisation in synchronisation with inhalation.

The liquid receptacle retains the liquid medicament that has passed through the apertures of the nozzle arrangement at the vicinity of the nozzle arrangement for subsequent atomisation. The receptacle need not be an enclosed chamber and it is not essential to fill the receptacle providing the liquid is retained at the inner surface of the nozzle arrangement. The use of an enclosed chamber may be a means of metering the dose of medicament. For this option, the rear of the liquid receptacle (6) is sealed with a membrane of microporous material (20) (or an additional nozzle array) which is capable of allowing the passage of air but not liquid. (See FIGS. 1a–1c) The enclosed chamber so formed defines the volume of a single dose of liquid medication. An amount of liquid in excess of this volume is brought into contact with the front nozzle array from, for example, a small feed tube, and the piezo-electric transducer is energised. Liquid is drawn into the chamber until full, while air is simultaneously expelled through the microporous membrane or rear nozzle array. The excitation voltage is switched off, the excess liquid is drawn off the surface of the nozzle array using, for example, the feed tube under negative pressure and the device is ready for use as an atomiser, having been fully primed. Subsequent excitation will empty the chamber of its contents in a fine spray of droplets.

DETAILED DESCRIPTION

Figure 1A:
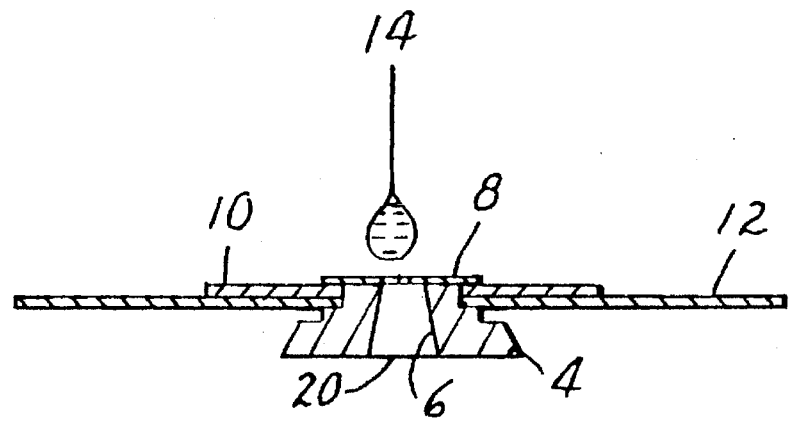
Figure 1B:
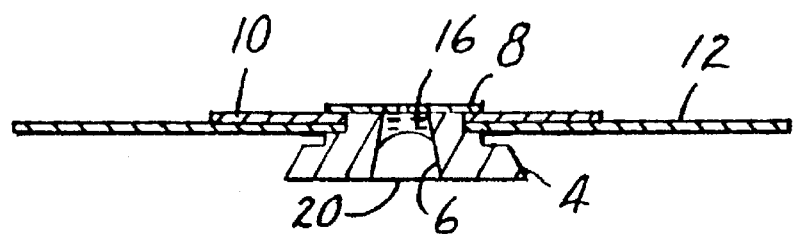
Figure 1C:
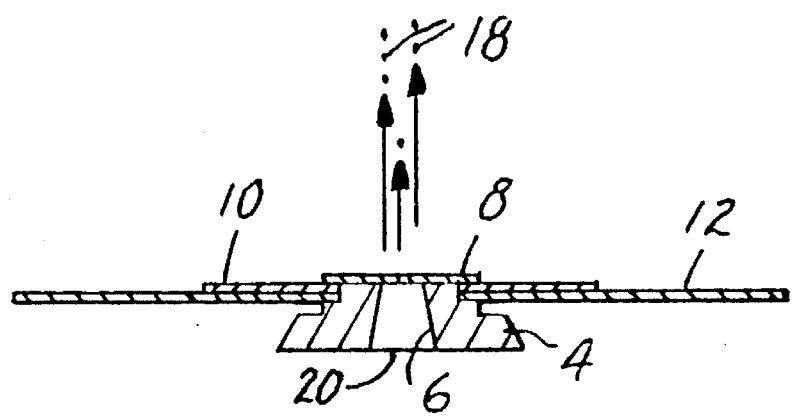

The invention will now be described with reference to the accompanying drawing in which FIGS. 1(a) to 1(c) illustrate an aerosol generator for use in an inhaler of the invention at different stages of operation.

The aerosol generator comprises a housing (4) defining a liquid receptacle (6) having at one end a nozzle array or arrangement (8). A vibrator element comprising a piezoelectric ring (10) mounted on a metal disc (12) is attached in close proximity to the nozzle array (8) such that ultrasonic energy from the vibrator element is transferred directly to the nozzle array (8). The diameter of the metal disc (12) is preferably about 20 mm and it is attached over a central portion of about 4 mm diameter. The vibrator element is generally driven at high frequency e.g. 10 to 500 kHz to provide a good flow rate through. In use, a drop (14) of liquid medicament is placed on the nozzle arrangement (8) and the vibrator element is energised to vibrate the nozzle arrangement (8). The vibration initially causes the liquid to pass through the apertures in the nozzle arrangement (8) into the liquid receptacle (6) as shown at (16) in FIG. 1(b). Thereafter, continued vibration, particularly at a high amplitude, causes emission of the medicament in the form of aerosolised droplets (as shown at (18) in FIG. 1(c)).

The aerosol generator may readily be incorporated into an inhaler having a mouthpiece or nasal adaptor, and optionally a venturi and-breath-actuated mechanism as disclosed in WO92/11050.

We claim:

1. An aerosol generator for dispensing droplets of liquid medicament, comprising:

a housing defining a liquid receptacle having an opening;

a nozzle arrangement comprising a plurality of orifices, said nozzle arrangement having an outer surface and an inner surface facing the interior of the liquid receptacle and covering said opening;

vibrating means for vibrating the nozzle arrangement;

means for introducing liquid medicament on the outer surface of the nozzle arrangement; and control means for controlling the vibrating means such that, when liquid medicament is introduced on the outer surface of the nozzle arrangement, the nozzle arrangement is vibrated with a first vibration having a first characteristic to cause the liquid medicament to enter the liquid receptacle through the orifices and is then vibrated with a second vibration having a second characteristic different from said first characteristic to cause the liquid medicament to be expelled from the orifices through the outer surface in the form of atomised droplets.

2. An aerosol generator as claimed in claim 1 wherein said vibrating means comprises a piezoelectric element associated with said nozzle arrangement such that excitation of said piezoelectric element causes vibration of said nozzle arrangement.

3. An aerosol generator as claimed in claim 2 wherein said piezoelectric element is in the form of a ring secured to a metal disc, the ring and metal disc each having a central opening to accommodate attachment of the piezo-electric element to the nozzle arrangement or to the liquid receptacle adjacent the nozzle arrangement.

4. An aerosol generator as claimed in claim 2 wherein said vibrating means comprises means to excite the piezo-electric element at a resonant frequency within the frequency range of from about 10 to about 500 kHz.

5. An aerosol generator as claimed in claim 1 wherein the diameter of the orifices is in the range of from about 2 to about 50 μm.

6. A method of dispensing droplets of liquid medicament comprising providing a liquid receptacle having an opening covered by a nozzle arrangement, the nozzle arrangement comprising a plurality of orifices and having an inner surface facing the interior of the liquid receptacle and an outer surface, introducing liquid medicament on the outer surface of the nozzle arrangement, vibrating the nozzle arrangement with a first vibration having a first characteristic such that the liquid medicament on the outer surface of the nozzle arrangement is caused to enter the liquid receptacle through the orifices, and thereafter vibrating the nozzle arrangement with a second vibration having a second characteristic different from said first characteristic such that the liquid medicament is expelled from the orifices through the outer surface in the form of atomised droplets.

7. An aerosol generator as claimed in claim 1 wherein said housing further comprises a membrane positioned at the end of said liquid receptacle opposite said opening, said membrane being made of a material which is capable of allowing the passage of air, but not liquid.

8. A method as claimed in claim 6 further comprising the step of positioning a membrane at the end of the liquid receptacle opposite the opening, the membrane being made of a material which is capable of allowing the passage of air, but not liquid.

* * * * *